United States Patent [19]

Davies et al.

[11] 4,125,413
[45] Nov. 14, 1978

[54] DISPERSION OF POLYCYCLIC VAT-DYE PIGMENT WITH N,N'-DISUBSTITUTED DIAMINOSTILBENE SULFONIC ACID FLUIDIZING AGENT

[75] Inventors: Peter K. Davies; James F. Stansfield; Arthur Topham, all of Manchester, England

[73] Assignee: Imperial Chemical Industries Limited, London, England

[21] Appl. No.: 795,302

[22] Filed: May 9, 1977

[30] Foreign Application Priority Data

Jun. 7, 1976 [GB] United Kingdom ............... 23431/76
Sep. 21, 1976 [GB] United Kingdom ............... 39093/76

[51] Int. Cl.$^2$ ............................................. C08K 5/34
[52] U.S. Cl. ........................... 106/308 Q; 106/308 M; 106/308 N; 542/461
[58] Field of Search ...................... 542/461, 430; 8/34, 8/1 W; 106/308 Q, 308 M, 308 N

[56] References Cited

U.S. PATENT DOCUMENTS

| | | | |
|---|---|---|---|
| 2,745,830 | 5/1956 | Siegrist | 542/461 |
| 2,846,397 | 8/1958 | Binningen | 542/461 |
| 3,193,548 | 7/1965 | Crounse et al. | 542/461 |
| 3,743,526 | 7/1973 | Zwahlen | 106/308 Q |
| 3,992,145 | 11/1976 | Coraor | 8/1 W |
| 4,001,035 | 1/1977 | Ito et al. | 106/308 M |
| 4,057,436 | 11/1977 | Davies et al. | 106/308 N |

FOREIGN PATENT DOCUMENTS 2,541,483 9/1975 Fed. Rep. of Germany.

OTHER PUBLICATIONS

A.P.C. Application of Wendt, Ser. No. 381,856, published 5/11/43.

*Primary Examiner*—Allen B. Curtis
*Assistant Examiner*—Raymond Covington
*Attorney, Agent, or Firm*—Cushman, Darby & Cushman

[57] ABSTRACT

The present invention relates to a fluidizing agent which is a substituted ammonium salt of an N,N'-disubstituted diaminostilbene sulphonic acid wherein there is at least one organic radical containing at least 2 carbon atoms attached to the nitrogen atom of the substituted ammonium ion. The agent is useful for improving the fluidity of a dispersion of a polycyclic vat dye pigment in an organic liquid.

10 Claims, No Drawings

DISPERSION OF POLYCYCLIC VAT-DYE PIGMENT WITH N,N'-DISUBSTITUTED DIAMINOSTILBENE SULFONIC ACID FLUIDIZING AGENT

This invention relates to novel substituted ammonium salts of substituted stilbene sulphonic acids and the use thereof as fluidising agents in dispersions.

It is disclosed in Offenlegungsschrift 2541483 that the fluidity of dispersions of solids in organic liquids can be enhanced by the addition of certain fluidising agents that are substituted ammonium salts of coloured acids, i.e. dyestuffs or pigments having at least one acidic group. However, problems are encountered in the selection of fluidising agents for any particular solid to be dispersed, normally a pigment or a dyestuff, because it is important that the agent should not mask or alter the shade of the solid and that it should be able to withstand the conditions to which the solid is subjected after application of the dispersion to a substrate. These problems arise particularly with stoving enamels based on such dispersions where, among the restricted range of substituted ammonium salts of coloured acids suitable for matching the shade of the pigment contained in the enamel, none are able to withstand the high temperatures involved in stoving, without severe discolouration. Such discolouration alters the shade of the enamel rendering it commercially unattractive.

We have now discovered that certain non-coloured acids will form substituted ammonium salts, similar to those described above, which act as fluidising agents in certain pigment dispersion systems in organic liquids.

According to the present invention we provide a fluidising agent which is a substituted ammonium salt of an N,N'-disubstituted diaminostilbene sulphonic acid wherein there is at least one organic radical containing at least 2 carbon atoms attached to the nitrogen atom of the substituted ammonium ion.

The substituted ammonium ion desirably contains at least 4, preferably 12 and more preferably between 16 and 80 carbon atoms. Particularly useful agents have a substituted ammonium ion containing either 3 or 4 organic chains containing in total at least 19 and preferably between 25 and 40 carbon atoms. It is further preferred that at least one of the chains is an alkyl or alkenyl group containing at least 8, more preferably at least 12 carbon atoms and especially between 12 and 20 carbon atoms. It is especially preferred that at least one such organic chain contains at least 16 carbon atoms.

The N,N'-disubstituted diaminostilbene sulphonic acid, hereinafter referred to as "the stilbene sulphonic acid", is preferably symmetrically substituted about the central —CH=CH— group of the stilbene molecule. There are preferably two sulphonic acid groups attached to different benzene rings in the ortho position, the amino groups being preferably attached to the benzene rings in the para position with respect to the central —CH=CH— group.

Preferred N-substituents for the diaminostilbene sulphonic acid are 4,6-disubstituted triazine-2-yl radicals having the general formula:

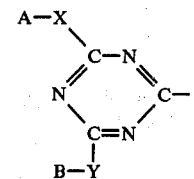

wherein
X and Y are each independently —S—; —O—; —NH— or —NR— wherein R is alkyl,
A is optionally substituted phenyl and
B is optionally substituted phenyl, optionally substituted alkyl, or where Y is NR-, Y and B together may form an optionally substituted aromatic or aliphatic ring, provided that both A and B are free from sulphonic acid groups.

Alternatively the stilbene sulphonic acids may comprise chains of two or more diaminostilbene sulphonic acid units linked together by triazinylene radicals and terminated at either end by a 4,6-disubstituted triazin-2-yl radical as defined hereinbefore.

The alkyl radical represented by R is preferably a lower alkyl radical, i.e. containing from 1 to 4 carbon atoms and as examples there may be mentioned methyl, ethyl and propyl radicals.

The optionally substituted phenyl radical represented by A or B is preferably phenyl itself or alkyl phenyl such as tolyl and ethyl-phenyl and the optionally substituted alkyl radical represented by B is preferably lower alkyl or substituted lower alkyl, wherein lower alkyl has the meaning defined hereinbefore, such as methyl, ethyl, the propyl radicals and hydroxyethyl.

As examples of the optionally substituted aromatic and aliphatic rings that can be formed by Y and B together when Y is NR there may be mentioned piperidine and morpholine and substituents thereof.

Particularly suitable fluidising agents are those in which X is —NH— or —NR— wherein R has the above defined meaning.

Whilst many of the fluidising agents may be fairly soluble in the organic liquid it is not essential that they are more than sparingly soluble.

The fluidising agents may be prepared by any of the conventional methods for preparing such salts such as by neutralising the stilbene sulphonic acid with the appropriate amine or substituted ammonium hydroxide or by reaction of the alkali metal salt of the stilbene sulphonic acid with the appropriate substituted ammonium halide. While the two reactants may be mixed in stoichiometric proportions this is not essential for the purpose of the invention and good results can be obtained with excess of either the amine, the substituted ammonium salt or the stilbene sulphonic acid (or its alkali metal salt).

As examples of the amines and substituted ammonium halides that may be used to form the fluidising agents there may be mentioned primary, secondary and tertiary amines and quaternary substituted ammonium salts such as butylamine, dibutylamine, octylamine, t-octylamine, cyclohexylamine, dodecylamine, octadecylamine, didodecylamine, N,N-dimethyloctadecylamine, cetyltrimethylammonium bromide, didodecyldimethylammonium chloride and dioctadecyldimethylammonium chloride.

Alternatively the amines or quaternary ammonium salts may contain polyester chains such as the amines and amine salts described in U.K. Patent Specification No. 1,373,660 especially the polyester amine condensates formed by the reaction between diamines and polyhydroxy stearic acid.

The amines and substituted ammonium salts may be cyclised wherein at least two of the organic chains are linked to form a ring containing the nitrogen atom which will form the charge centre of the substituted ammonium ion. The ring or rings so formed may be aliphatic rings such as piperidine and morpholine or aromatic rings such as pyridine and as examples of such amines or salts there may be mentioned N-cetyl pyridinium salts and N-cetylpiperidine.

One or more of the organic radicals attached to the N-atom of the amine or substituted ammonium ion may be substituted by aromatic groups such as phenyl and substituted phenyl radicals which are free from acidic groups, e.g. benzyldimethyloctadecylammonium chloride. Alternatively one or more of the organic radicals may contain other non-acidic substituents such as hydroxy groups, e.g. octadecyl-bis-(2hydroxyethyl)amine, amino or substituted amino, e.g. 3(N-octadecyl-N-hydroxyethylamino)-propyl-N',N'-bis(2-hydroxyethyl)amine, 3-octadecylaminopropylamine and N,N'-di-o-tolylguanidine, thus forming polyamines, one or more of the amino groups of which may be involved in forming the substituted ammonium ion.

As examples of the stilbene sulphonic acids which may be used to form the fluidising agent of the invention there may be mentioned 4,4'-bis-(4-anilino-6-β-hydroxyethylamino-s-triazin-2-ylamino)stilbene-2,2'-disulphonic acid, 4,4'-bis-(4-anilino-6-methylamino-s-triazin-2-yl-amino)stillbene-2,2'-disulphonic acid, 4,4'-bis-(4-anilino-6-methoxy-s-triazinyl-2-yl-amino)stilbene-2,2'-disulphonic acid, 4,4'-bis-(4,6-dianilino-s-triazin-2-yl-amino)stilbene-2,2'-disulphonic acid, 4,4'-bis-(4-p-toluidino-6-diethylamino-s-triazine-2-ylamino)stilbene-2,2'-disulphonic acid. 4,4'-bis-(4-anilino-6-morpholino-s-triazin-2-ylamino)stilbene-2,2'-disulphonic acid and 2,4-bis-[4-(4,6-dianilino-s-triazin-2-ylamino)-2,2'-disulpho-stilben-4'-ylamino]-6-anilino-triazine or the alkali metal salts thereof.

According to a further feature of the invention there is provided a dispersion of a polycyclic vat dye pigment in an organic liquid containing a polymeric or resinous dispersing agent and a fluidising agent as hereinbefore defined.

By polycyclic vat dye pigment is meant a substantially insoluble coloured compound containing at least 4 fused rings and at least one quinone group capable of reduction to a leuco compound. A preferred vat dye pigment (hereinafter referred to as 'the pigment') for use in the above defined composition is one containing from 6 to 8 fused rings and within this selection especial mention may be made of flavanthrone, indanthrone and dibromoanthanthrone.

The dispersing agent may be any of those used conventionally in the preparation of dispersions of pigments, dyestuffs and other solids in organic liquids and especially those used in the manufacture of inks and paints. The preferred dispersing agents are those developed for use in the preparation of concentrated non-aqueous dispersions of pigments and dyestuffs directly from crude colour.

The organic liquid may be any in which the pigment is substantially insoluble although it is preferred to use liquid aromatic hydrocarbons or liquid aliphatic or aromatic chlorinated hydrocarbons.

The dispersion of this invention can be obtained by any of the conventional and well known methods of preparing dispersions. Thus the pigment, the organic liquid, the fluidising agent and the dispersing agent may be mixed in any order and the mixture then subjected to a mechanical treatment to reduce the particle size of the solid, for example by ball milling, bead milling or gravel milling until the dispersion is formed, in which the particle size of the solid is less than 10 microns and preferably less than 1 micron.

Alternatively, where the dispersing agent and the fluidising agent are completely soluble in the organic liquid, the pigment can be treated to reduce its particle size independently or in admixture with either the organic liquid or both of the dispersing and fluidising agents, and the other ingredient or ingredients then added following which dispersion can be obtained by stirring the mixture.

A dispersion obtained in this way and comprising the pigment in finely divided form and the dispersing and fluidising agents is a further feature of the invention.

The amount of dispersing agent is such as corresponds to between 25% and 400% by weight and the amount of the fluidising agent is such as corresponds to between 0.5% and 50% by weight based on the weight of the pigment, the preferred ranges being between 75% and 200% and 5% and 10% respectively. The composition preferably contains between 10% and 20% by weight of the pigment based on the total weight of the dispersion.

As examples of the dispersing agents that may be employed in the dispersion of this invention there may be mentioned the dispersing agents that are described in U.K. Patent Specifications Nos. 139,341, 1,373,660, 1,313,745, U.K. Patent Specification No. 1,445,135, U.S. Patent Nos. 3,741,941 3,788,996, 3,704,255, 3,817,944 and 3,654,771, and in German Patent Application No. 2,350,454, acrylate and methacrylate polymers and copolymers, alkyd resins, polyester resins, modified alkyd resins, urethanes, urethane oils, tars and pitches such as gilsonite as used in the preparation of newsprint inks, which dispersing agents are more particularly described in Offenlegungsschrift 2,541,483. For the preparation of a dispersion according to the invention which is to be used in the preparation of paints and enamels, it is preferred to use a dispersing agent which has been specially developed to be compatible with the other resins and binders used in paints and enamels. Of particular interest for this purpose are the dispersing agents which are described and claimed in U.K. Patent Specifications Nos. 1,108,261 and 1,159,252 and the agents developed from these which are described and claimed in U.K. Specification No. 1,346,298.

In British Specification No. 1,108,261 there are described and claimed dispersants having the formula:

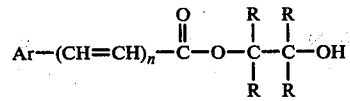

wherein Ar is an aromatic group, $n$ is 1 or 0, from 2 to 3 R groups are individually hydrogen, methyl or ethyl and the remaining R group or groups individually or the remaining group R — C — C — R in combination provides a solvatable chain-like component of at least 12 links. The Specification defines the term "solvatable" and gives examples of the solvatable chain-like components having at least 12 links which are present in the said dispersants.

Also in British Specification No. 1,159,252 there are described dispersants comprising an addition polymer chain solvated by an organic liquid and having attached thereto at least one group of the formula:

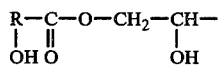

wherein R an an aliphatic radical which may contain one or more additional hydroxy groups. The Specification also defines the term "solvated" and gives examples of the addition polymer chains. Specification No. 1,346,298 describes and claims dispersants which are the reaction products of compounds of the formula:

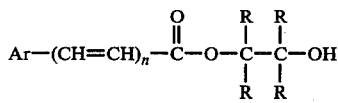

wherein Ar is an aromatic group, $n$ is 0 or 1, from 2 to 3 R groups are individually hydrogen, methyl and ethyl and the remaining R in combination provides a solvatable chain-like component of at least 12 links, with an organic monoisocyanate or with an organic diisocyanate which has already been or is simultaneously or subsequently reacted with an alcohol or amine so that in effect it behaves as a monoisocyanate.

As examples of the organic liquid which may be used to form the dispersion of the invention there may be mentioned esters, such as dialkyl phthalates, alkyd resins and heat bodied linseed oils used as lithographic varnish media, aliphatic alcohols such as ethanol and propanol, ketones such as acetone, methyl ethyl ketone and diethyl ketone, aliphatic hydrocarbons such as petroleum fractions boiling between 60° C and 200° C, white spirit, n-hexane, cyclohexane and mineral oils such as spindle oil and sump oil as used in the preparation of newsprint inks. Preferred organic liquids are however aromatic hydrocarbons such as benzene, xylene, mesitylene and in particular toluene and chlorinated hydrocarbons such as chlorobenzene, carbon tetrachloride and perchloroethylene.

The invention is illustrated by the following Examples in which the proportions of ingredients are measured in parts by weight.

EXAMPLE 1

A solution of 38 parts of 4,4'-bis-(4-anilino-6-β-hydroxyethylamino-s-triazin-2-ylamino)-stilbene-2,2'-disulphonic acid in 19 parts of triethanolamine and 200 parts of water at 90° C is stirred whilst a solution of 30.5 parts of cetyltrimethylammonium bromide in 91.5 parts of hot water is added. After stirring for 1/2 hour at 90° C and cooling, the solid is filtered off, washed and dried.

EXAMPLE 2

To a solution of 4 parts of sodium 4,4'-bis(4-anilino-6-methylamino-s-triazin-2-ylamino)-stilbene 2,2'-disulphonate in 20 parts of water at 90° C is added 17 parts of a 25% solution of cetyl trimethylammonium bromide in hot water. After stirring for 30 minutes at 90° C and cooling, the solid is filtered off, washed and dried.

EXAMPLE 3

To a solution of 10 parts of sodium 4,4'-bis-(4-anilino-6-methoxy-s-triazin-2-ylamino)stilbene 2,2'-disulphonate in 100 parts of water at 90° C is added 17 parts of a 25% solution of cetyl trimethyl ammonium bromide in hot water. After stirring for 30 minutes at 90° C and cooling the solid is filtered off, washed and dried.

EXAMPLE 4

To a solution of 10 parts of the sodium salt of the acid used in Example 1 in 50 parts of water at 90° C is added 9.7 parts of didodecyldimethyl ammonium chloride as a 75% solution in isopropanol (Arquad 2C: RTM). After stirring for 30 minutes at 90° C and cooling the solid is filtered off, washed and dried.

EXAMPLE 5

To a suspension of 10 parts of the free acid used in Example 1 in 400 parts of water at 90° C is added 40 parts of a 16.4% solution of N,N-dimethyloctadecylamine (Armeen DMHT:RTM) in hot dilute acetic acid. After stirring for 30 minutes at 90° C and cooling the solid is filtered off, washed and dried.

EXAMPLE 6

To a solution of 40 parts of the free acid used in Example 1 in 200 parts of water at 90° C and 20.3 parts of triethanolamine is added 51 parts of dioctadecyl dimethylammonium chloride as a 75% solution in isopropanol (Arquad 2HT: RTM). After stirring for 30 minutes at 90° C and cooling the solid is filtered off, washed and dried.

EXAMPLE 7

To a solution of 10 parts of the sodium salt of the free acid used in Example 1 in 400 parts water at 90° C there is added 3.64 parts of N,N-bis-(2-hydroxyethyl)-octadecylamine (Ethomeen T/12: RTM) as a solution in hot dilute acetic acid. After stirring for 30 minutes at 90° C and cooling the solid is filtered off, washed and dried.

EXAMPLE 8

To a solution of 5 parts of sodium 4,4'-bis-(4,6-dianilino-s-triazin-2-ylamino)stilbene-2,2'-disulphonate in water at 100° C is added 4.25 parts of cetyltrimethyl ammonium bromide in 12.75 parts of hot water. After stirring for 30 minutes at 90° C and cooling the solid is filtered off, washed and dried.

EXAMPLE 9

To a solution of 5 parts of sodium 4,4'-bis-(4-p-toluidino-6-diethylamino-s-triazin-2-ylamino)-stilbene-2,2'-disulphonate in 400 parts water at 90° C is added 12 parts of a 25% solution of cetyl trimethyl ammonium bromide in hot water. After stirring for 30 minutes at 90° C and cooling the solid is filtered off, washed and dried.

EXAMPLE 10

To a solution of 1 part of sodium 4,4'-bis-(4-anilino-6-morpholino-s-triazin-2-ylamino)-stilbene-2,2'-disulphonate in 100 parts of water at 90° C is added 7 parts of a 25% solution of cetyl trimethylammonium bromide in hot water. After stirring for 30 minutes at 90° C and cooling, the solid is filtered off, washed and dried.

EXAMPLE 11

To a solution of 5 parts of the sodium salt of the free acid used in Example 1 in 100 parts of water at 90° C is added a 25% solution of cetyl pyridinium bromide in hot water until precipitation is complete. After stirring for 30 minutes at 90° C and cooling, the solid is filtered off, washed and dried.

EXAMPLE 12

To a solution of 5 parts sodium 4,4'-bis(4,6-di-N-methylanilino-s-triazin-2-ylamino)-stilbene-2,2'-disulphonate in 200 parts of water at 90° C is added 17 parts of a 25% solution of cetyl trimethylammonium bromide in hot water. After stirring for 30 minutes at 90° C and cooling, the solid is filtered off, washed and dried.

EXAMPLE 13

A mixture of 1.5 parts of a 50% solution in xylene of a copolymer of styrene/ethylhexylacrylate/hydroxyisopropylmethacrylate/methacrylamide/glycidyl methacrylate, in the proportions of 26/40/25/5/4 by weight, esterified with p-aminobenzoic acid in the presence of dimethyl dodecylamine, (as described in B.P. No. 1,108,261), 0.2 parts of the fluidising agent described in Example 1, 7.3 parts of xylene and 1 part of pigmentary flavanthrone is ball milled for 16 hours to give a fluid dispersion of the pigment which is suitable for use in indistrial paint. When the fluidising agent described in Example 1 is omitted a thick dispersion is obtained.

The following table gives further examples of dispersions of the invention, where the presence of the fluidising agent as defined herein improves the fluidity of the dispersion, which are obtained by milling together the pigment and the number of parts thereof listed in column 2 of the Table, the agents and number of parts thereof listed in columns 3 and 4 of the table and sufficient of the organic liquids listed in column 5 of the table to bring the total weight to 10 parts.

| Ex. | Pigment and amount thereof | Dispersing Agent and amount thereof | Fluidising Agent and amount thereof | Organic Liquid |
|---|---|---|---|---|
| 14 | 2 parts of flavanthrone | 2 parts of 50% solution described in Example 13 | 0.2 part of the fluidising Agent prepared according to Example 1 | xylene |
| 15 | " | 1.5 parts of 50% solution described in Example 13 | " | " |
| 16 | " | 3 parts of 50% solution described in Example 13 | " | " |
| 17 | " | 1.5 parts of 50% solution described in Example 13 | 0.1 part of the fluidising Agent prepared according to Example 1 | " |
| 18 | 2 parts 4,10 Di-bromoanthanthrone | 1 part of 50% solution described in Example 13 | 0.2 part of the fluidising Agent prepared according to Example 1 | " |
| 19 | " | 2 parts of 50% solution described in Example 13 | " | " |
| 20 | 1 part of flavanthrone | 2 parts of 50% solution described in Example 13 | 0.2 part of the fluidising Agent prepared according to Example 1 | " |
| 21 | " | " | 0.2 part of Fluidising Agent prepared according to Ex.2 | " |
| 22 | " | " | 0.2 part of Fluidising Agent prepared according to Ex.3. | " |
| 23 | " | " | 0.2 part of Fluidising Agent prepared according to Ex.4. | " |
| 24. | 1 part of flavanthrone | 2 parts of 50% solution described in Example 13 | 0.2 part of Fluidising Agent prepared according to Ex.5 | xylene |
| 25 | " | " | 0.2 part of Fluidising Agent prepared according to Ex.6 | " |
| 26 | " | " | 0.2 part of Fluidising Agent prepared according to Ex.7 | " |
| 27 | " | " | 0.2 part of Fluidising Agent prepared according to Ex.8 | " |
| 28 | 2 parts of indanthrone | 3 parts of 50% solution described in Ex.13 | 0.2 part of Fluidising Agent prepared according to Ex.1 | " |
| 29 | 1 part of flavanthrone | 2 parts of 50% solution described in Ex.13 | 0.2 part of Fluidising Agent prepared according to Ex.9 | " |
| 30 | " | " | 0.2 part of Fluidising Agent prepared according to Ex.10 | " |
| 31 | " | " | 0.2 part of Fluidising Agent prepared according to Ex.11 | " |
| 32 | " | " | 0.2 part of Fluidising Agent prepared according to Ex.12 | " |
| 33 | " | 1 part of a gum rosin known as Portugese Y Grade | 0.2 part of Fluidising Agent prepared according to Ex.1 | " |
| 34 | " | 1 part of the adduct of nonylphenol with 8 molecules of ethylene oxide. | " | " |
| 35 | 1 part of flavanthrone | 1.7 parts of a 60% soln. in isopropyl acetate of a copolymer of 42 parts of methyl methacrylate, 40 parts of 2-ethylhexyl methacrylate and 18 parts of 2-hydroxyethyl methacrylate. | 0.2 parts of Fluidising Agent prepared according to Ex.1 | xylene |
| 36 | " | 1 part of a hydrocarbon resin produced by polymerising an unsaturated $C_5$ hydrocarbon fraction. | " | " |
| 37 | " | 1 part of polyvinylpyrrolidone, grade K30 as | " | ethanol |

-continued

| Ex. | Pigment and amount thereof | Dispersing Agent and amount thereof | Fluidising Agent and amount thereof | Organic Liquid |
|---|---|---|---|---|
| 38 | " | marketed by General Aniline and Film Corpn. 1 part of an adduct of of molecular weight 1500 from iso-octanol and a mixture of equal parts by weight of ethylene oxide and propylene oxide. | " | toluene |
| 39 | " | 1 part of chlorinated rubber of molecular weight 100,000 | " | " |
| 40 | " | 1 part of Resin MS2, a polymerised ketone resin | " | " |
| 41 | " | 1 part of Epikote 828, a diphenylolpropane based epoxy resin. | " | " |
| 42 | 1 part of flavanthrone | 1 part of a copolymer of vinylidene chloride, acrylonitrile and methyl methacrylate. | 0.2 part of Fluidising Agent prepared according to Ex.1. | tetrahydrofuran |
| 43 | " | 1 part of a rosin modified phenol-formaldehyde resin known as "Mitchanol 37" (RTM) and marketed by W.A. Mitchell and Smith Ltd | " | toluene |
| 44 | " | 1 part of an alkyd resin containing 68% linseed oil fatty acids, 20% phthalic anhydride and pentaerythritol | " | " |
| 45 | " | 1 part of a linear polycaprolactone of molecular weight 2000 known as "CAPA 420" (RTM) and marketed by Interox Chemicals Ltd. | " | " |
| 46 | 1 part of flavanthrone | 1 part of an oxypropylated glycerol of molecular weight 312 | " | toluene |
| 47 | " | 1 part of a block copolymer comprising 90 parts by weight of propylene oxide, 10 parts by weight ethylene oxide and having a molecular weight of 1940 known as "Pluronic L61" (RTM) marketed by Wyandotte Chemical Corporation. | " | " |
| 48 | 1 part of flavanthrone | 1.7 parts of a 60% solution in isopropyl acetate of a copolymer of 42 parts methyl methacrylate and 18 parts hydroxyethyl methacrylate. | 0.2 parts of Fluidising Agent prepared according to Example 1. | isopropyl-acetate |
| 49 | " | " | " | methyl-isobutyl-ketone- |

EXAMPLE 50

5 Parts of the product obtained by reacting 2 moles of 4,4'-diaminostilbene-2,2'-disulphonic acid with 3 moles of cyanuric chloride and finally with excess aniline (the reaction being effected by adding the acid to a suspension of the cyanuric chloride in water below 5° C at pH 6-7, raising the temperature to 90° C, adding excess aniline, filtering the product, washing with dilute hydrochloric acid until free from aniline and drying is stirred in 400 parts of water and heated to 95° C. 26 Parts of 25% solution of cetyltrimethylammonium bromide in water is added and the precipitate formed is washed by decantation and dried at 100° C.

EXAMPLE 51

A mixture of 1 part of pigmentary flavanthrone, 2 parts of the 50% solution described in Example 13, 0.2 parts of the fluidising agent prepared according to Example 50 and 6.8 parts of xylene is ball-milled for 16 hours to give a fluid dispersion of the pigment which is suitable for use in industrial paint.

Substituted ammonium salts of 4,4'-bis-(4-anilino-6-β-hydroxyethylamino-s-triazin2-ylamino)-stilbene-2,2'-disulphonic acid with the amines listed in Examples 52 to 63 below were prepared by neutralising the stilbene sulphonic acid with the equivalent quantity of the amine shown. The ammonium salts so prepared were incorporated into dispersions in the proportions shown in Examples 64 to 75 using the method of Example 13. The dispersions were in each case more fluid than equivalent dispersions from which the substituted ammonium salts had been omitted.

| Example | Amine |
|---|---|
| 52 | butylamine |
| 53 | dibutylamine |
| 54 | octylamine |
| 55 | t-octylamine |
| 56 | 2-ethylhexylamine |
| 57 | N,N'-di-o-tolyl guanidine |
| 58 | 3-octadecylaminopropylamine |
| 59 | morpholine |
| 60 | piperidine |
| 61 | cyclohexylamine |
| 62 | N,N-dimethylcyclohexylamine |
| 63 | The amine prepared according to Example 1 of U.S. Pat. Specification No. 1373660. |

| Ex. | Pigment and amount thereof | Dispersing Agent and amount thereof | Fluidising Agent and amount thereof | | Organic Liquid and amount thereof |
|---|---|---|---|---|---|
| 64 | 1 part of flavanthrone | 2 parts of 50% soln described in Example 13 | 0.2 part of fluidising agent prepared according to Example | 52 | 6.8 parts of xylene |
| 65 | " | " | " | 53 | " |
| 66 | " | " | " | 54 | " |
| 67 | " | " | " | 55 | " |
| 68 | " | " | " | 56 | " |
| 69 | " | " | " | 57 | " |
| 70 | " | " | " | 58 | " |
| 71 | " | " | " | 59 | " |
| 72 | " | " | " | 60 | " |
| 73 | " | " | " | 61 | " |
| 74 | " | " | " | 62 | " |
| 75 | " | " | " | 63 | " |

We claim:

1. A dispersion of a polycyclic vat-dye pigment in an organic liquid containing a polymeric or resinous dispersion agent and a fluidising agent which is a substituted ammonium salt of a N,N'-disubstituted diaminostilbene sulphonic acid wherein the substituted ammonium ion contains a total of from 2 to 80 carbon atoms in from 1 to 4 organic radicals attached to the central nitrogen atom.

2. A dispersion according to claim 1 wherein there is a total of from 16 to 80 carbon atoms in the substituted ammonium ion.

3. A dispersion according to claim 1 wherein there is a total of from 19 to 40 carbon atoms in 3 or 4 organic chains attached to the central nitrogen atom.

4. A dispersion according to claim 1 wherein at least one of the organic radicals is an alkyl or an alkenyl group containing from 12 to 20 carbon atoms.

5. A dispersion according to claim 1 wherein the N,N'-disubstituted diaminostilbene sulphonic acid comprises a single diaminostilbene sulphonic acid substituted in each amino group by a 4:6-disubstituted triazine-2-yl radical having the formula:

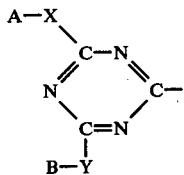

wherein
X and Y are each independently selected from —S—; —O—; —NH—; and —NR— wherein R is alkyl,
A is phenyl or substituted phenyl,
B is selected from phenyl, substituted phenyl, alkyl and substituted alkyl,
and where Y is —NR—, Y and B together may form an optionally substituted aromatic or aliphatic ring provided that both A and B are free from sulphonic acid groups.

6. A dispersion according to claim 5 wherein the N,N'-disubstituted diaminostilbene sulphonic acid comprises a chain of two or more diaminostilbene sulphonic acid units linked together by triazinylene radicals and terminated at either end by a 4–6 disubstituted triazine-2-yl radical as defined.

7. A dispersion according to claim 1 wherein the pigment is selected from flavanthrone, indanthrone and dibromo anthanthrone.

8. A dispersion according to claim 1 wherein the organic liquid is selected from aromatic hydrocarbons, aromatic chlorinated hydrocarbons and aliphatic chlorinated hydrocarbons.

9. A dispersion according to claim 1 wherein the polymeric or resinous dispersing agent is a compound of the formula:

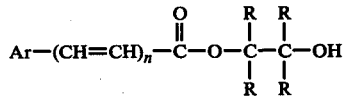

wherein Ar is an aromatic group, $n$ is 0 or 1, from 2 to 3 R groups are individually hydrogen, methyl and ethyl and the remaining R group or groups individually or the remaining R — C — C — R in combination provides a solvatable chain-like component of at least 12 links.

10. A dispersion of flavanthrone in xylene containing dissolved therein
(i) a copolymer of styrene ethylhexylacrylate, hydroxyisopropylmethacrylate, methacrylamide and glycidylmethacrylate in the proportions 26:40:25:5:4 by weight esterified with p-aminobenzoic acid, and
(ii) the cetyl trimethylammonium salt of 4,4'-bis-(4-anilino-6-β-hydroxyethylamino-s-triazin-2-ylamino)stilbene-2,2'-disulphonic acid.

* * * * *